United States Patent
Wan et al.

(10) Patent No.: US 10,001,472 B2
(45) Date of Patent: Jun. 19, 2018

(54) 3D DETERMINATION OF CELL CHIRALITY

(71) Applicant: Rensselaer Polytechnic Institute, Troy, NY (US)

(72) Inventors: Qun Wan, Watervliet, NY (US); Amanda S. Chin, Glendale, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days. days.

(21) Appl. No.: 15/191,787

(22) Filed: Jun. 24, 2016

(65) Prior Publication Data

US 2016/0377603 A1 Dec. 29, 2016

Related U.S. Application Data

(60) Provisional application No. 62/184,293, filed on Jun. 25, 2015.

(51) Int. Cl.
*G01N 33/50* (2006.01)

(52) U.S. Cl.
CPC ..... *G01N 33/5091* (2013.01); *G01N 33/5005* (2013.01)

(58) Field of Classification Search
None
See application file for complete search history.

(56) References Cited

U.S. PATENT DOCUMENTS

2015/0004643 A1  1/2015  Vunjak-Novakovic et al.

OTHER PUBLICATIONS

Wan L. et al. Cell Chirality: Emergence of Asymmetry from Cell Culture. Philosophical Transactions B 371(1710)1-9, Dec. 19, 2016. (Year: 2016).*
Miyakoshi J. Effects of Static Magnetic Fields at the Cellular Level. Biophysics & Molecular Biology 87(2-3)213-223, 2004. (Year: 2004).*
Topman G. et al. A New Technique for Studying Directional Cell Migration... Micron 51:9-12, Aug. 2013 (Year: 2013).*
Wan L. et al. Micropatterned Mammalian Cells Exhibit Phenotype Specific Left-Right Asymmetry. PNAS 108(30)12295-12300, Jul. 26, 2011. (Year: 2011).*

* cited by examiner

*Primary Examiner* — Ralph J Gitomer
(74) *Attorney, Agent, or Firm* — Hoffman Warnick LLC (57) ABSTRACT

Described herein is a method for determining chirality of a cell. The method includes culturing a cell on a base layer having a cell growth material. The method includes forming a top layer on the base layer after the cell has attached to the base layer, the top layer having a cell growth material. The base layer and the top layer form a graded 3D substrate. The intrinsic bias of the cell is determined from the directionality of spontaneous cell rotation.

9 Claims, 4 Drawing Sheets

3D DETERMINATION OF CELL CHIRALITY

CROSS-REFERENCE TO RELATED APPLICATIONS

This application claims the benefit of U.S. Provisional Patent Application No. 62/184,293, filed Jun. 25, 2015, which is hereby incorporated herein as though fully set forth. This invention was made with government support under CMMI-1254656 awarded by the National Science Foundation (NSF). The government has certain rights in the invention.

FIELD OF THE INVENTION

The present disclosure generally relates to cell chirality and analysis thereof.

BACKGROUND OF THE INVENTION

Detecting differences at the cellular level is an ongoing problem which, if successfully addressed, could help solve several prevalent ailments, including cancers and prenatal diseases.

Normal tissue function requires appropriate cell positioning and directional motion. This property, known as chirality, can be altered by genetic and environmental factors, leading to, for example, birth defects and tumor formation.

Current methods to diagnose cancer are based on biomarkers, imaging, and analysis of tissue specimens. In most cases, the findings from one assay (such as imaging) are corroborated by other assays (such as pathological evaluation of biopsy samples).

Chirality is often known as left-right (LR) asymmetry in the development of numerous living organisms, including climbing plants, helices of snail shells, and the human body. Genetic diseases and prenatal exposure to teratogens can cause birth defects in laterality. The LR asymmetry has been studied in animal embryos, which are difficult to control and are not necessarily representative of human condition. Recent studies focused on directional nodal flow driven by primary cilia, pH gradients resulting from asymmetric expression of ion channels, and asymmetric vesicular transport.

The initiation of chirality in development is often first observed in populations of cells of the same type, such as snail embryonic cells at 4-cell and 8-cell stages and mouse cells at embryonic nodes. 2-dimensional (2D) cultures used for determining cell chirality are described in US 2015/0004643.

However, 2D cultures do not fully represent the dynamics of tissue polarization and cell-cell interactions during tissue formation in vivo. Moreover, it is not possible to measure chirality of certain cells with 2D cultures. It would be desirable to have 3-dimensional (3D) cultures to more accurately simulate the complexity of cellular behavior and morphology during natural tissue development.

SUMMARY

Described herein is a method for determining chirality of a cell. The method includes culturing a cell on a base layer having a cell growth material. The method includes forming a top layer on the base layer after the cell has attached to the base layer, the top layer having the cell growth material. The base layer and the top layer form a 3D substrate. The directionality of the cell is determined. The directionality of the cell is measured from a nucleus of the cell to an organelle of the cell along a plurality of orthogonal sections of the substrate.

There is described a method of diagnosing a disease. The method includes culturing a cell on a base layer having a cell growth material and forming a top layer on the base layer after the cell has attached to the base layer, the top layer having the cell growth material. The base layer and the top layer form a three dimensional substrate. The directionality of the cell is determined by measuring from a nucleus of the cell to an organelle of the cell along a plurality of orthogonal sections of the substrate. The method includes culturing a diseased cell on a base layer having the cell growth material and forming a top layer on the base layer after the diseased cell has attached to the base layer, the top layer having the cell growth material. The base layer and the top layer form a three dimensional substrate. The directionality of the diseased cell is determined by measuring from a nucleus of the diseased cell to an organelle of the diseased cell along a plurality of orthogonal sections of the substrate. The directionality of the cell is compared and correlated with the directionality of the diseased cell by finding an opposite directionality of the cell compared to the diseased cell.

There is provided a method of diagnosing a cancer including culturing a cell of a first type on a base layer having a cell growth material, forming a top layer on the base layer after the cell of the first type has attached to the base layer, the top layer having the cell growth material, wherein the base layer and the top layer form a three-dimensional substrate. The directionality of the cell of the first type is determined by measuring from a nucleus of the cell of the first type to an organelle of the cell of the first type along a plurality of orthogonal sections of the substrate. The method includes culturing a cancer cell of the first type on a base layer having the cell growth material and forming a top layer on the base layer after the cancer cell of the first type has attached to the base layer, the top layer having the cell growth material, wherein the base layer and the top layer form a three dimensional substrate. The directionality of the cancer cell of the first type is determined by measuring from a nucleus of the cancer cell of the first type to an organelle of the cancer cell of the first type along a plurality of orthogonal sections of the substrate. The directionality of the cell of the first type with the directionality of the cancer cell of the first type is compared and a change in the directionality of the cell of the first type compared to the directionality of the cancer cell of the first type is correlated.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

During tumor development there is a loss of polarity in epithelial cells resulting in structural and organization disorders. Chirality, or left-right (LR) asymmetry, is an intrinsic property of mammalian cells that is vital for normal tissue morphogenesis. Chirality is phenotype specific and there is a distinct difference in LR bias between normal and cancer cells. 3D culture systems may offer more accurate simulation of the complexity of cellular behavior during development in vivo.

The present disclosure is based at least in part on the surprising discovery that directional cell movement on a 3-dimensional (3D) substrate is not random but, rather, significantly biased towards either left or right orientation (chirality) in a way that was specific to the cell phenotype.

In brief, cells cultured on a 3D substrate exhibit chiral morphogenesis that can be readily determined by analysis of cell rotation. In studies of various cell types, it was observed that cell chirality was defined by cell phenotype, and that loss of actin but not microtubule function could reverse the counter clockwise (CCW) cell chirality. Experiments presented herein demonstrate that normal and cancer cells of the same type can have opposite chirality; the chirality of normal human cells can be reverted by exposure to mutagens; actin inhibitors can reverse cell chirality; and cancer cell chirality depends on actin function.

Shown herein are experiments with 3D substrates. In embodiments, cells can be cultured on a 3D substrate at a density of about 2,000 to about 20,000 cells·cm$^{-2}$. The cell density in experiments described herein was in the range of about 6,000 to about 13,000 cells·cm$^{-2}$, which was dependent on the desired microtissue size. The chiral alignment and biased migration of the cells on the 3D substrate was determined by fluorescent time lapse imaging and phase contrast imaging. Videos were created by taking time lapse images for at least 2 hours with an interval of one minute. Directional motion of cultured cells was observed. Cells were shown to migrate within the 3D substrate taking either left or right direction (i.e., clockwise or counterclockwise on ring patterns) or complex direction. It was also shown that cell chirality related to actin function.

Described herein is a method for a 3D micro-assay to determine cellular chirality (LR asymmetry). In various embodiments, a simple and highly accurate in vitro platform can be used to study the initiation of chiral morphogenesis and identify genetic, biochemical and environmental factors leading to malformations.

Substrate

As described herein, a substrate is provided. The substrate can be of any material suitable for cell growth (see e.g., Freshney 2010 Culture of Animal Cells: A Manual of Basic Technique and Specialized Applications, 6th Ed., Wiley-Blackwell, ISBN-10: 9780470528129; Helgason and Miller 2004 Basic Cell Culture Protocols, 3d Ed., Humana Press, ISBN-10: 1588292843). Exemplary embodiments include a gelatinous protein mixture secreted by Engelbreth-Holm-Swarm (EHS) mouse sarcoma cells available from Corning Life Sciences under the name MATRIGEL®, or from Trevigan Inc. under the name Cultrex BME. In embodiments, poly-ethylene glycol (PEG) at various molecular weight can be used as a substrate.

The substrate can be coated with, for example, an attachment protein. Exemplary attachment proteins include fibronectin.

The substrate can include a first layer or base layer at a desired concentration of cell growth material. After attachment (incubation time of about 1 hour) of the cell, a second layer is deposited over the first layer thereby embedding the cells in a 3D substrate. The second layer contains cell growth material. In embodiments, the concentration of the cell growth material in the base layer is higher than the concentration of cell growth material in the top layer. The base layer of the substrate can be coated with a substance to facilitate cell attachment (e.g., fibronectin). In embodiments, the substrate has a depth of from about 500 µm to about 3,500 µm.

Cell

As described herein, a cell can be cultured in a 3D substrate so as to determine chirality. A cell can be any cell of interest. A cell can be any cell for which determination of chirality is desired. A cell can be an animal cell. A cell can be a mammalian cell. A cell can be derived from an animal, including, but not limited to, mammals, reptiles, and avians, more preferably horses, cows, dogs, cats, sheep, pigs, and chickens, and most preferably human. A cell can be, for example, an exocrine secretory epithelial cell, a hormone secreting cell, an epithelial cell lining a closed internal body cavity, a keratinizing epithelial cell, a wet stratified barrier epithelial cell, a sensory transducer cell, an autonomic neuron cell, a sense organ and peripheral neuron supporting cell, a central nervous system neuron, a central nervous system glial cell, a lens cell, a metabolism and storage cell, a barrier function cell (e.g., lung, gut, exocrine glands or urogenital tract), a kidney cell, an extracellular matrix cell, a contractile cell, a blood and immune system cell, a pigment cell, a germ cell, a nurse cell, or an interstitial cell. For example, a cell can be an endothelial cell, a fibroblast cell, a stem cell (e.g., a mesenchymal stem cell), a skeletal muscle cell, an osteoblast cell, or a myoblast cell.

A cell can be isolated, purified, or cultured by a variety of means known to the art Methods for the isolation and culture of cells are discussed in, for example, Vunjak-Novakovic and Freshney (2006) Culture of Cells for Tissue Engineering, Wiley-Liss, ISBN 0471629359.

A cell can be a wild type cell or a transgenic cell. Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Chirality

As described herein, chirality can be determined for a cell cultured on a 3D substrate. Directionality can be measured with respect to the nucleus of the cell to an organelle in the cell of the cell along an x-axis. The directionality can also be determined by tracking the rotation of the cell in phase contrast time-lapse. Organelles used to determine rotation include Gogli apparatus, endopalasmic reticulum, etc. Determination of chirality can be according to analysis of an image of a cell on the 3D substrate. The image can be, for example, a phase contrast image and confocal microscopy. Analysis to determine chirality of a cell in a 3D substrate can be done by time-lapse analysis.

A cell cultured in a 3D substrate can undergo rotation (chirality) or no rotation. Direction of rotation was categorized into clockwise (CW), counterclockwise (CCW), complex rotation, and no rotation. Complex rotation is identified when the cell exhibits a switching of direction repeatedly or if the cell rotates through several planes instead of around the z-axis. Rotation of a cell on a 3D substrate can be indicative of chirality of the cell, as described herein.

Cells can be cultured on any 3D substrate at any density suitable for determination of rotation. Cell density can be optimized according to factors including, but not limited to, cell type, substrate type, or culture conditions. In some embodiments, cells can be cultured on a 3D substrate at a density of about 2,000 cells·cm$^{-2}$ to about 20,000 cells·cm$^{-2}$.

Algorithm

Described herein is an algorithm for determining cell chirality. Such algorithm can be used to determine cell chirality from, for example, phase contrast images of orthogonal sections of the 3D substrate.

The following describes an image-processing algorithm to determine cellular chirality (clockwise (CW), counterclockwise (CCW), complex or no rotation) on 3D substrates towards potential applications in disease detection and drug screening. The algorithm can be used with, for example, methods for cell printing, cultivation and the acquisition of phase contrast images described herein. A program implementing such algorithm can provide automated determination of the chirality of patterned cells.

An algorithm to determine cellular chirality from, for example, phase contrast images of cells cultured on 3D substrates. The description below is based on 3D substrates. One of ordinary skill will understand such techniques can be applied to other 3D substrates discussed herein.

Figure 1:
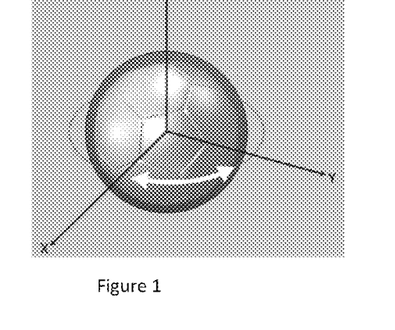
FIG. 1 is an illustration of the rotational path of cells cultured on a 3D substrate.

A representation is shown in FIG. 1 with the arrow indicating the rotational bias of either clockwise or counterclockwise rotation around the z-axis.

Correlation to Disease

A determination of chirality can be correlated to a disease or disorder. For example, a change in chirality from that normally associated with a particular cell type can indicate a disease or disorder. Such correlation can provide a protocol for diagnosing or confirming a diagnosis of a disease or disorder.

A change in chirality can be, for example, an opposite chirality from that normally associated with a particular cell type. A change in chirality can be, for example, an exaggerated or amplified chirality from that normally associated with a particular cell type.

For example, a determination of a change in chirality from that normally associated with a particular cell type can indicate the tested cell is a cancerous cell. For example, a determination of a change in chirality as compared to the chirality normally associated with a particular cell type can indicate the tested cell is a cancerous cell.

Cancer types generally include carcinoma (malignant tumors derived from epithelial cells, including breast, prostate, lung and colon cancer); sarcoma (malignant tumors derived from connective tissue, or mesenchymal cells); lymphoma and leukemia (malignancies derived from hematopoietic cells); germ cell tumor (tumors derived from totipotent cells); cancer stem cells, blastic tumor or blastoma (tumor resembling an immature or embryonic tissue). Cancers include, but are not limited to, gastrointestinal tumors, cancer of liver and biliary tract, pancreatic cancer, prostatic cancer, testicular cancer, colorectal cancer, lung cancer, breast cancer, cutaneous melanoma, ovarian cancer, uterine cancer, cervical cancer, endometrial cancer, cancer of the head and neck, brain cancer, bladder cancer, leukemia, non-Hodgkin lymphoma, sarcomas and osteosarcomas, Kaposi sarcoma, AIDS-related Kaposi sarcoma, and renal carcinoma. A cell type, as used herein, can be any cell associated with a cancer described above. A determination of a change in chirality from that normally associated with a particular cell type can indicate the tested cell is a cancerous cell of a type described above.

Birth defects can be associated with genetic diseases or prenatal exposure to teratogens, which impact cell chirality. A determination of a change in chirality as compared to the chirality normally associated with a particular cell type can indicate the tested cell has been exposed to a teratogen. A determination of a change in chirality as compared to the chirality normally associated with a particular cell type can indicate the tested cell has a genetic abnormality associated with a genetic disease or disorder in a subject.

Screening

Determination of chirality of a cell cultured on a 3D substrate can be used in screening protocols. For example, methods described herein can be used for screening effects of candidate agents on cell chirality.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example:

ChemBridge, Princeton BioMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Preferably, initial screening is performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 angstroms to about 15 angstroms.

Kits

Also provided are kits. Such kits can include a 3D substrate or components for production thereof, and, in certain embodiments, instructions for administration. Such kits can facilitate performance of the methods described herein. When supplied as a kit, the different components of the composition can be packaged in separate containers and admixed immediately before use. Components include, but are not limited to containers for 3D substrates, cell culture reagents, or analytical software.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web-site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

Figure 2:
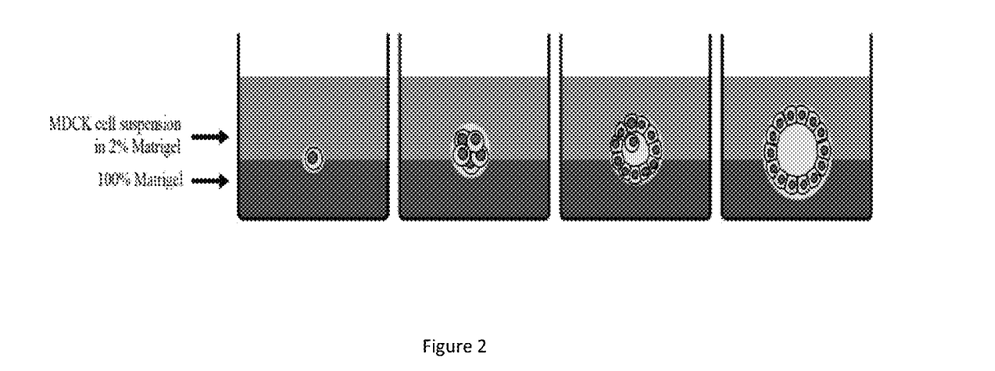
FIG. 2 is cross-sectional view of cells cultured on a 3D substrate.

The cell line used was Madin-Darby canine kidney (MDCK) epithelial cells. The 3D substrate culture system included a base layer was composed of 100% MATRIGEL®. The base layer was seeded with a single cell suspension of MDCK epithelial cells. After cell attachments to the base layer, a top layer was generated by overlaying culture with 2% MATRIGEL®. This is shown in FIG. 2.

Self-organization of the epithelial cells during microtissue development was observed using phase contrast imaging and confocal microscopy. The cells were stained with DAPI (4',6-diamidino-2-phenylindole), Phalloidin, and ZO-1 antibody.

Time-lapse images were collected for at least 2 hours at intervals of 1 minute over a period of 6 days. Videos were processed in ImageJ and analyzed for quantification of collective rotational direction. Direction of rotation was categorized into clockwise (CW), counterclockwise (CCW), complex rotation, and no rotation. Phase-contrast images of microtissue development from a single cell embedded within the multilayer MATRIGEL® system over time. Confocal slices of the microtissue in MATRIGEL® revealed a spherical structure containing a lumen.

Figure 3:
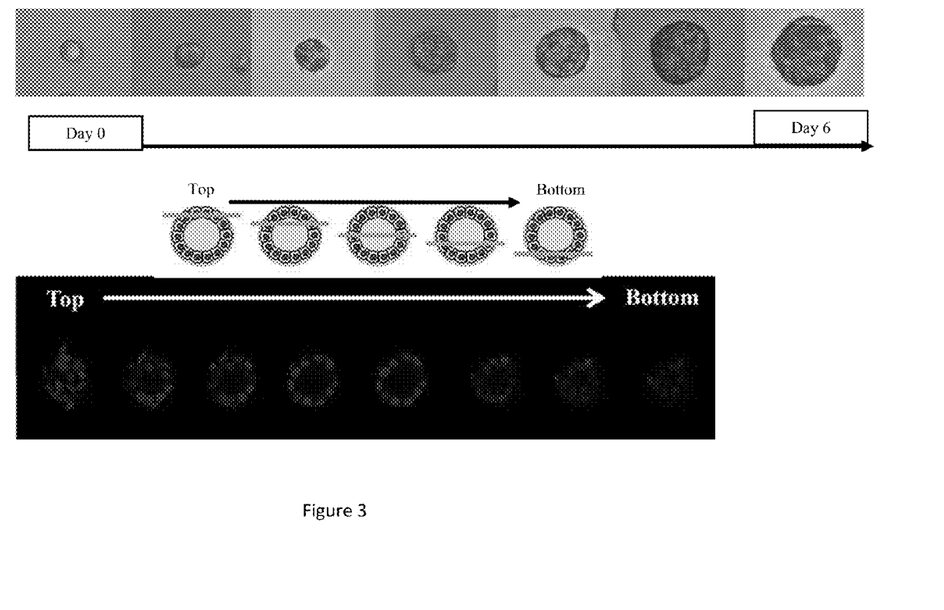
FIG. 3 shows time-lapse images of cells cultured on a 3D substrate over a period of time.

The cells were sectioned orthogonally which confirmed the structure of the microtissue was a hollowed sphere. Phase-contrast images of microtissue development from a single cell embedded within the multilayer MATRIGEL® system over time. FIG. 3 shows the growth of the microtissue over the 6 days. The orthogonal slices are shown from top to bottom. Confocal microscopy imaging revealed morphological architecture of the microtissue spheres. The luminal spheroid structure exhibited higher expression of actin along the apical surface, assembly was further confirmed by expression of laminin V only at the exterior of the spheroid.

The cells embedded within the 3D substrate showed biased rotation as the cells proliferated. The rotation was predominantly counterclockwise which was in agreement with 2D studies. The chirality arises in single cells embedded in the 3D substrate.

Figure 4:
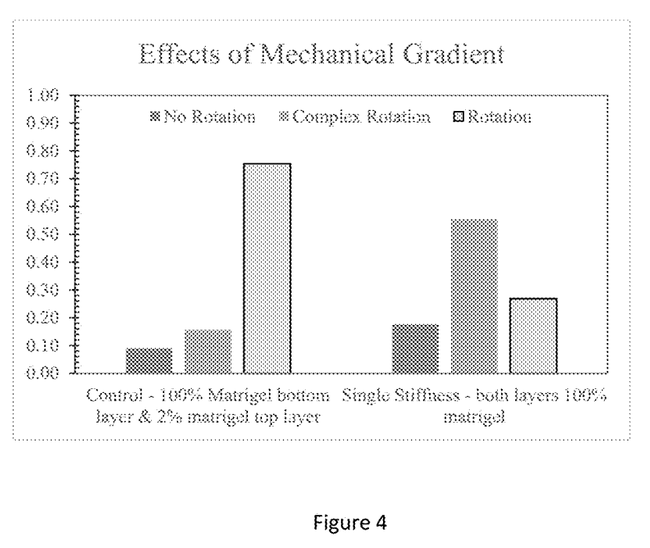
FIG. 4 shows the effect of rotation versus of cell growth material concentration in a 3D substrate.

The influence of a mechanical gradient on the rotational behavior of the microtissues using a single concentration of MATRIGEL® was examined and the results are shown in FIG. 4. Majority of multicellular constructs rotated about the z-axis when cultured within the bilayers of differing MATRIGEL® concentration. In the uniform top and base layer system, there was a dominance of complex rotation which illustrated the necessity of a gel gradient created by the bilayer of differing concentrations in order for the chirality to be revealed in the in-plane rotation of the cells.

Figure 5:
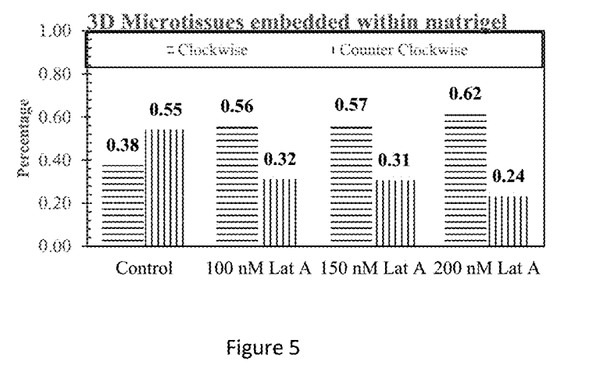
FIG. 5 shows the effect of Latrunculin A on rotation direction.

Latrunculin A was used to study the role of actin function in left right asymmetry. Latrunculin A is a drug which inhibits actin polymerization. Latrunculin A caused a reversal of chirality in which the MDCK cells were greatly biased toward clockwise chirality. Higher concentrations of Latrunculin A caused an increasing clockwise chirality. This is shown in FIG. 5. These studies are consistent with 2D studies.

Chirality is an inherent cellular property that is an acute factor in coordinated rotation. Without a gradient in the MATRIGEL®, the cells would not be able to perform in plane (x-y) rotation.

Figure 6:
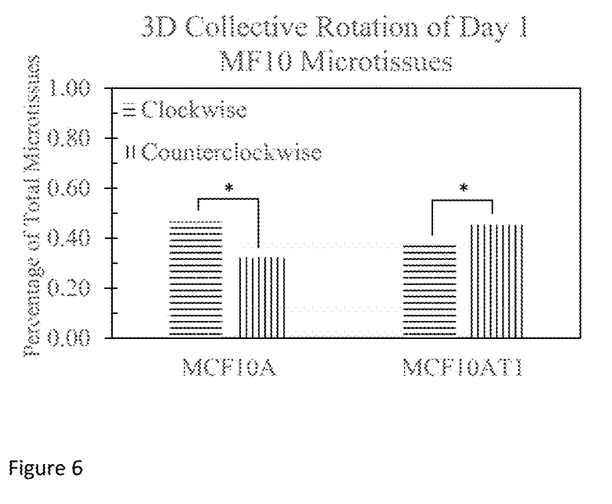
FIG. 6 shows the 3D collective rotation of Day 1 MCF microtissues.

The apparently normal MCF-10A has a clockwise dominant chirality, while its cancerous variant, MCF10AT1 has a counter clockwise dominance. These results are consistent with 2D studies reported before for normal skin fibroblasts and those from cancerous skin. This is shown in FIG. 6.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

The invention claimed is:

1. A method for determining chirality of a cell comprising:
culturing a cell on a base layer having a cell growth material;
forming a top layer on the base layer after the cell has attached to the base layer, the top layer having a cell growth material, wherein the base layer and the top layer form a three dimensional substrate;
culturing the cell in the three dimensional substrate;
measuring a direction of rotation from a nucleus of the cell to an organelle of the cell along a plurality of orthogonal sections of the three dimensional substrate;
determining a chirality of the cell based on the direction of rotation.

2. The method of claim 1, wherein the cell growth material comprises a gelatinous protein mixture secreted by mouse sarcoma cells.

3. The method of claim 1, wherein the cell growth material comprises poly ethylene glycol.

4. The method of claim 1, wherein culturing a cell on the base layer comprises culturing a plurality of cells on the base layer at a density of: (i) about 2,000 cells·cm$^{-2}$ to about 20,000 cells·cm$^{-2}$.

5. The method of claim 1, wherein the three dimensional substrate has a depth of from 500 μm to 3500 μm.

6. The method of claim 1, wherein the organelle is a Gogli apparatus.

7. The method of claim 1, wherein the organelle is an endoplasmic reticulum.

8. The method of claim 1, wherein the top layer has a lower concentration of cell growth material than the base layer.

9. The method of claim 1, wherein the cell is an animal cell selected from the group consisting of an exocrine secretory epithelial cell, a hormone secreting cell, an epithelial cell lining a closed internal body cavity, a keratinizing epithelial cell, a wet stratified barrier epithelial cell, a sensory transducer cell, an autonomic neuron cell, a sense organ and peripheral neuron supporting cell, a central nervous system neuron, a central nervous system glial cell, a lens cell, a metabolism and storage cell, a barrier function cell, a kidney cell, an extracellular matrix cell, a contractile cell, a blood and immune system cell, a pigment cell, a germ cell, a nurse cell, an interstitial cell, an endothelial cell, a fibroblast cell, a stem cell, a skeletal muscle cell, an osteoblast cell and a myoblast cell.

* * * * *